United States Patent
Fertig et al.

(10) Patent No.: US 7,638,553 B2
(45) Date of Patent: Dec. 29, 2009

(54) HYDROXAMATES, THEIR MANUFACTURE AND USE AS PHARMACEUTICAL AGENTS

(75) Inventors: Georg Fertig, Penzberg (DE); Frank Herting, Sindelsdorf (DE); Matthias Koerner, Antdorf (DE); Manfred Kubbies, Penzberg (DE); Anja Limberg, Penzberg (DE); Ulrike Reiff, Penzberg (DE); Ulrich Tibes, Starnberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 472 days.

(21) Appl. No.: 11/628,725

(22) PCT Filed: Jun. 13, 2005

(86) PCT No.: PCT/EP2005/006293

§ 371 (c)(1),
(2), (4) Date: Dec. 5, 2006

(87) PCT Pub. No.: WO2005/121119

PCT Pub. Date: Dec. 22, 2005

(65) Prior Publication Data

US 2008/0139640 A1   Jun. 12, 2008

(30) Foreign Application Priority Data

Jun. 14, 2004   (EP) .................................. 04013862

(51) Int. Cl.
*A61K 31/381* (2006.01)
*C07D 333/22* (2006.01)
(52) U.S. Cl. ........................................ 514/448; 549/72
(58) Field of Classification Search ................ 514/448; 549/72
See application file for complete search history.

(56) References Cited

FOREIGN PATENT DOCUMENTS

| WO | WO 01/38322 | 5/2001 |
|----|-------------|--------|
| WO | WO 03/011851 | 2/2003 |
| WO | WO 03/076395 | 9/2003 |
| WO | WO 03/087066 | 10/2003 |

*Primary Examiner*—Taofiq A Solola
(74) *Attorney, Agent, or Firm*—George W. Johnston; Patricia S. Rocha-Tramaloni; Gene J. Yao

(57) ABSTRACT

Objects of the present invention are the compounds of formula (I), their pharmaceutically acceptable salts, enantiomeric forms, diastereoisomers and racemates, the preparation of the above-mentioned compounds, medicaments containing them and their manufacture, as well as the use of the above-mentioned compounds in the control or prevention of illnesses such as cancer.

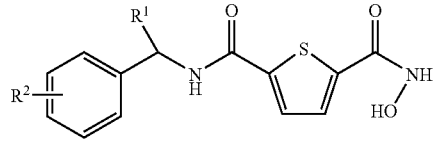

20 Claims, No Drawings

HYDROXAMATES, THEIR MANUFACTURE AND USE AS PHARMACEUTICAL AGENTS

The present invention relates to novel hydroxamates and to their (R)- and (S)-enantiomers and racemates, to a process for their manufacture, medicaments containing them and their manufacture as well as the use of these compounds as pharmaceutically active agents.

Transcriptional regulation is a major event in cell differentiation, proliferation, and apoptosis. Transcriptional activation of a set of genes determines cell destination and for this reason transcription is tightly regulated by a variety of factors. One of its regulatory mechanisms involved in the process is an alteration in the tertiary structure of DNA, which affects transcription by modulating the accessibility of transcription factors to their target DNA segments. Nucleosomal integrity is regulated by the acetylation status of the core histones. In a hypoacetylated state, nucleosomes are tightly compacted and thus are nonpermissive for transcription. On the other hand, nucleosomes are relaxed by acetylation of the core histones, with the result being permissiveness to transcription. The acetylation status of the histones is governed by the balance of the activities of histone acetyl transferase (HAT) and histone deacetylase (HDAC). Recently, HDAC inhibitors have been found to arrest growth and apoptosis in several types of cancer cells, including colon cancer, T-cell lymphoma, and erythroleukemic cells. Given that apoptosis is a crucial factor for cancer progression, HDAC inhibitors are promising reagents for cancer therapy as effective inducers of apoptosis (Koyama, Y., et al., Blood 96 (2000) 1490-1495).

Several structural classes of HDAC inhibitors have been identified and are reviewed in Marks, P. A., et al., J. Nat. Cancer Inst. 92 (2000) 1210-1216. More specifically, WO 98/55449, U.S. Pat. No. 5,369,108, WO 01/38322, WO 01/70675, WO 02/22577, WO 03/011851, WO 03/066579, WO 03/075929, WO 03/076395, WO 03/076400, WO 03/076401, WO 03/076421, WO 03/076422, WO 03/076430, WO 03/076438, WO 03/087066 and WO 2004/013130 report alkanoyl, alkylenyl, alkenylenyl, aryl, heteroaryl, benzyl, biaryl and cinnamyl hydroxamates with HDAC inhibitory activity.

However there remains a need for new compounds with improved therapeutic properties, such as enhanced activity, decreased toxicity, better solubility and improved pharmacokinetic profile, to name only a few. The present invention relates to hydroxamates and to their (R)- and (S)-enantiomers and racemates of formula I

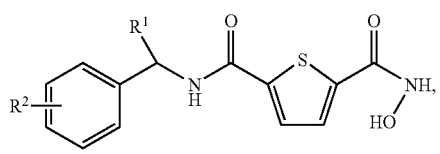

formula I wherein
$R^1$ is alkyl, which is optionally substituted one or several times by halogen;
$R^2$ is —$SF_5$;
—O-alkyl; the alkyl groups being optionally substituted one or several times by halogen;
—$S(O)_2$—$CF_3$;
—S(O)-alkyl;
—S-alkyl; the alkyl groups being optionally substituted one or several times by halogen;
—$S(O)_2$-aryl;
—S(O)-aryl;
—S-aryl;
—$S(O)_2$-benzyl;
—S(O)-benzyl; or
—S-benzyl; and
the pharmaceutically acceptable salts thereof.

One embodiment of the invention relates to hydroxamates and to their (R)- and (S)-enantiomers and racemates of formula I, wherein
$R^2$ is —$SF_5$;
—O—$CF_3$;
—O—$CHF_2$;
—$S(O)_2$—$CF_3$;
—S(O)-alkyl;
—S-alkyl; the alkyl groups being optionally substituted one or several times by halogen;
—$S(O)_2$-aryl;
—S(O)-aryl;
—S-aryl;
—$S(O)_2$-benzyl;
—S(O)-benzyl; or
—S-benzyl;
and pharmaceutically acceptable salts thereof.

The compounds according to this invention are inhibitors of histone deacetylase (HDAC) and therefore possess antiproliferative activity. Objects of the present invention are the compounds of formula I and their pharmaceutically acceptable salts, diastereoisomers, racemates and especially their enantiomeric forms, the preparation of the compounds, medicaments containing such compounds and the manufacture of such medicaments as well as the use of such compounds in the control or prevention of illnesses, especially of illnesses and disorders as mentioned below or in the manufacture of corresponding medicaments.

Examples of tumors which may be treated with such compounds or medicaments are colon cancers, breast carcinoma (including advanced breast cancer), lung cancer (e.g. adenocarcinoma and including non-small cell lung cancer), prostate cancer including advanced disease, pancreatic cancers, hematopoetic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MSD), tumors of mesenchymal origin, melanomas, teratocarcinomas, neuroblastomas, gliomas, benign tumors of the skin (e.g. keratoacanthomas), kidney carcinoma, ovary carcinoma, bladder carcinoma and epidermal carcinoma.

As used herein, the term "alkyl" means a saturated, straight-chain or branched-chain hydrocarbon containing from 1 to 6, preferably from 1 to 3, carbon atoms, such as methyl, ethyl, n-propyl, isopropyl, n-butyl, 2-butyl, t-butyl. Said alkyl group being optionally substituted by one or several halogen atoms, such as chlorine or fluorine, preferably by fluorine. Examples of substituted alkyl groups are difluoromethyl, trifluoromethyl, 2,2,2-trifluoroethyl and perfluoroethyl.

The term "halogen" as used herein denotes fluorine, chlorine and bromine, preferably fluorine and chlorine.

The term "aryl" as used herein denotes phenyl which may be optionally substituted one to three times by alkyl, halogen, —CN, —C(O)OH, —C(O)$CH_3$, —$NH_2$, —$CH_2NH_2$, —$CH_2OH$, or —O-alkyl, preferably by alkyl or halogen. Alkyl and halogen are defined as above; the alkyl groups being optionally substituted one or several times by halogen.

The term "benzyl" as used herein denotes a —CH$_2$-phenyl group wherein the phenyl may be optionally substituted one to three times by alkyl, halogen, —CN, —C(O)OH, —C(O) CH$_3$, —NH$_2$, —CH$_2$NH$_2$, —CH$_2$OH, or —O-alkyl, preferably by alkyl or halogen. Alkyl and halogen are defined as above, the alkyl groups being optionally substituted one or several times by halogen.

In the compounds of formula I, R$^1$ is preferably methyl, ethyl or trifluoromethyl especially methyl.

A further embodiment are compounds of formula I wherein R$^2$ is trifluoromethoxy, trifluoromethylsulfanyl, trifluoromethylsulfinyl and trifluoromethylsulfonyl especially trifluoromethoxy and trifluoromethylsulfanyl.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium, and quaternary ammonium hydroxides, such as for example, tetramethylammonium hydroxide. The chemical modification of a pharmaceutical compound (i.e., a drug) into a salt is a technique well known to pharmaceutical chemists to obtain improved physical and chemical stability, hygroscopicity, flowability and solubility of compounds. See, e.g., Stahl, P. H., and Wermuth, G., (editors), Handbook of Pharmaceutical Salts, Verlag Helvetica Chimica Acta (VHCA), Zürich, (2002) or Bastin, R. J., et al., Organic Proc. Res. Dev. 4 (2000) 427-435.

An embodiment of the invention are the compounds of formula I, wherein
R$^1$ is methyl.

Another embodiment of the invention are the compounds of formula I, wherein
R$^2$ is —O-alkyl wherein the alkyl group is substituted one to three times by fluorine; and
—S-alkyl wherein the alkyl group is substituted one to three times by fluorine.

Another embodiment of the invention are the compounds of formula I, wherein
R$^1$ is methyl; and
R$^2$ is —O-alkyl wherein the alkyl group is substituted one to three times by fluorine; and
—S-alkyl wherein the alkyl group is substituted one to three times by fluorine.

Another embodiment of the invention are the compounds of formula I, wherein
R$^2$ is —SF$_5$;
—O—CF$_3$;
—O—CHF$_2$;
—S(O)$_2$—CF$_3$;
—S(O)-alkyl; or
—S-alkyl; the alkyl groups being optionally substituted one or several times by halogen.

Another embodiment of the invention are the compounds of formula I, wherein
R$^2$ is —S(O)$_2$-aryl;
—S(O)-aryl;
—S-aryl;
—S(O)$_2$-benzyl;
—S(O)-benzyl; or
—S-benzyl.

Another embodiment of the invention are the compounds of formula I, wherein
R$^2$ is —OCF$_3$;
—SCF$_3$; or
—SCH$_3$.

Still another embodiment of the invention are the compounds of formula I, wherein
R$^1$ is methyl; and
R$^2$ is —OCF$_3$;
—SCF$_3$; or
—SCH$_3$.

Such compounds are for example:
thiophene-2,5-dicarboxylic acid 2-hydroxyamide 5-{[1-(4-trifluoromethoxy-phenyl)-ethyl]-amide};
thiophene-2,5-dicarboxylic acid 2-hydroxyamide 5-{[1-(3-trifluoromethoxy-phenyl)-ethyl]-amide};
thiophene-2,5-dicarboxylic acid 2-hydroxyamide 5-{[1-(4-methylsulfanyl-phenyl)-ethyl]-amide};
thiophene-2,5-dicarboxylic acid 2-hydroxyamide 5-{[1-(3-trifluoromethylsulfanyl-phenyl)-ethyl]-amide}; and
thiophene-2,5-dicarboxylic acid 2-hydroxyamide 5-{[1-(4-trifluoromethylsulfanyl-phenyl)-ethyl]-amide}.

Still another embodiment of the invention are the compounds of formula I, wherein
R$^1$ is methyl; and
R$^2$ is —SF$_5$;
—O—CF$_3$;
—O—CHF$_2$;
—S(O)$_2$—CF$_3$; or
—S(O)-alkyl; the alkyl groups being optionally substituted one or several times by halogen.

Another embodiment of the invention are the compounds of formula I, wherein
R$^1$ is methyl; and
R$^2$ is —S(O)$_2$-aryl;
—S(O)-aryl; or
—S-aryl.

Such a compound is for example:
Thiophene-2,5-dicarboxylic acid 2-{[1-(4-benzenesulfonyl-phenyl)-ethyl]-amide}-5-hydroxyamide Another embodiment of the invention are the compounds of formula I, wherein
R$^1$ is methyl; and
R$^2$ is —S(O)$_2$-benzyl;
—S(O)-benzyl; or
—S-benzyl.

Yet another embodiment of the invention is the process for the manufacture of the compounds of formula I, and especially their (R)- and (S) enantiomers, by reacting a compound of formula IV

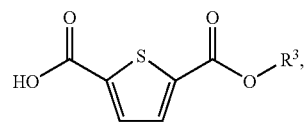

formula IV wherein
R$^3$ is an alkyl group;
with a racemic, or enantiomerically pure (R)- or (S)-amine of the formula III

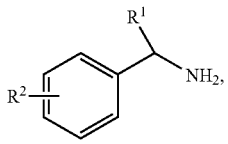

formula III wherein
R¹ and R² are defined as above for formula I,
in the presence of a suitable activating agent,
to give a compound of formula V

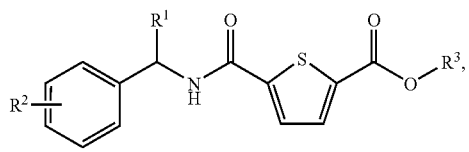

formula V which is subsequently treated with hydroxylamine to give the respective compound of formula I; and if desired, transforming said compound into its pharmaceutically acceptable salt.

The present compounds of formula I, or a pharmaceutically acceptable salt thereof, may be prepared by any process known to be applicable to the preparation of chemically-related compounds. Such processes, when used to prepare a hydroxamate of the formula I, or a pharmaceutically acceptable salt thereof, are illustrated by the following representative examples in which, unless otherwise stated, R¹ and R² have any of the meanings defined hereinbefore. Necessary starting materials may be obtained by standard procedures of organic chemistry. The preparation of such starting materials is described within the accompanying examples. Alternatively necessary starting materials are obtainable by analogous procedures to those illustrated which are within the ordinary skill of an organic chemist.

One method for the manufacture of compounds of formula I is shown in the following general reaction scheme 1 and represents also an embodiment of the invention:

Scheme 1

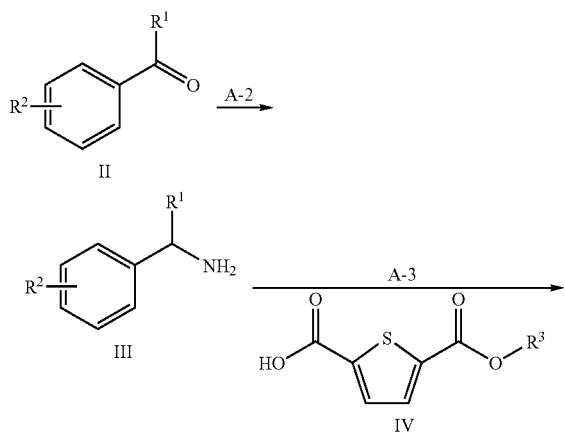

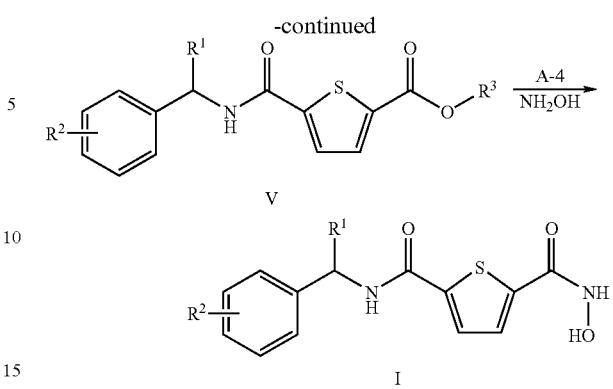

In scheme 1, R¹ and R² are defined as for formula I and R³ is alkyl or optionally substituted benzyl.

Ketones of the general formula II, wherein R¹ and R² have the meaning defined hereinbefore, are reduced to amines of formula III via the corresponding imines. Then the amides of formula V are formed by activation of the thiophenedicarboxylate of formula IV (R³ is Me) and subsequent treatment with amines of formula III. The final products are obtained after treatment of methyl esters of formula V with hydroxylamine, or its hydrochloride, to give the respective compounds of formula I; and if desired, said compound can be transformed into its pharmaceutically acceptable salt.

(A) This method for the production of compounds of formula I will be illustrated here:

(A-1) Ketones of formula II, wherein R¹ and R² have the meaning defined hereinbefore, are commercially available or can be prepared for example as follows:

(A-1-1) Ketones of formula II, wherein R¹ has the meaning defined hereinbefore and R² is an S(O)₂-aryl group or an S-aryl group can be prepared from halogen-substituted acetophenones (X-phenyl-C(O)-Me) or from acetyl-substituted phenylsulfonylchlorides (Cl—S(O)₂-phenyl-C(O)-Me) by treatment with suitable aryl-thioles or by a Friedel-Crafts type reaction applying suitable aryl compounds as described e.g. in Shulda, V. G., et al., J. Org. Chem. 68 (2003) 5422-5425 or Marquie, J., et al., J. Org. Chem. 66 (2001) 421.

(A-1-2) Ketones of formula II, wherein R¹ has the meaning defined hereinbefore and R² is an S-benzyl group can be prepared from halogen-substituted acetophenones (X-phenyl-C(O)-Me) by treatment with suitable benzyl-thioles as described e.g. in Howbert, J. J., et al., Synthetic Commun. 20 (1990) 3193-3200.

Ketones of formula II, wherein R¹ has the meaning defined hereinbefore and R² is an —S(O)₂-benzyl group can be prepared from acetyl-substituted phenylsulfonylchloride (Cl—S(O)₂-phenyl-C(O)-Me) by treatment with suitable benzyl-halogenides, benzyl-Grignard reagents or toluene derivatives as described in e.g., Sun, X. H., et al., Synthetic Commun. 28 (1998) 1785-1791; Gilman, H., et al., J. Am. Chem. Soc. 51 (1929) 3501-3508, or Alo, B. I., et al., J. Chem. Soc., Perkin Trans. 1 (1990) 1611-1614.

(A-2) Amines of formula III, wherein R¹ and R² have the meaning defined hereinbefore, can be prepared for example by reductive animation of the corresponding ketones of general formula II, but other methods may be useful as well and are well known to those skilled in the art.

This reaction is typically carried out as a one-pot reaction with the formation of the imine and its subsequent reduction to the amine taking place in the same reaction vessel. The reaction mixture usually contains a source of ammonia as for example but not limiting to NH$_4$OAc and a reducing agent as for example but not limiting to sodium cyanoborohydride and is heated in a suitable solvent as e.g. methanol.

Another method for the preparation of amines of general formula III is the addition of a Grignard reagent R$^1$—MgBr or an organolithium compound Li—R$^1$, with R$^1$ as defined hereinbefore, to an aromatic nitrile of the general formula R$^1$-Ph-CN and subsequent reduction of the imine (as e.g. described in Synth. Commun. 28 (1998) 4067).

(A-3) Compounds of formula V, wherein R$^1$ and R$^2$ have the meaning defined hereinbefore, can be prepared from compounds of formula III and compounds of formula IV wherein R$^3$ is alkyl or benzyl.

This reaction typically involves a two-step one-pot procedure.

In the first step, the carboxylic acid of the formula IV becomes activated. The activation reaction is carried out in an inert solvent or diluent, for example, in dichloromethane, dioxane, or tetrahydrofuran, in the presence of an activating agent. Such activated acid derivatives are, for example, an acyl halide (e.g. acyl chloride) formed by the reaction of the acid and an inorganic acid chloride, (e.g. thionyl chloride); a mixed anhydride, formed for example by the reaction of the acid and a chloroformate (e.g. isobutyl chloroformate); an active ester, formed for example by the reaction of the acid and a phenol (e.g. pentafluorophenol); an active ester, formed by the reaction of the acid and N-hydroxybenzotriazole; an acyl azide, formed for example by the reaction of the acid and an azide (e.g. diphenylphosphoryl azide); an acyl cyanide, formed for example by the reaction of an acid and a cyanide (e.g. diethylphosphoryl cyanide); or the product of the reaction of the acid and a carbodiimide (e.g. dicyclohexylcarbodiimide), or the product of the reaction of the acid and bis-(2-oxo-3-oxazolidinyl)-phosphorylchloride. The reaction is carried out between –30° C. and 60° C., conventionally at or below 0° C.

In the second step, the amine of the general formula III, in which R$^1$ and R$^2$ have the meaning defined hereinbefore, is added to the solution, at the temperature used for the activation, and the temperature is slowly adjusted to ambient temperature. An appropriate scavenger base like e.g. triethylamine, or diisopropylethylamine may be added to the reaction mixture. These methods are well known to those skilled in the art. In principle, all methods for the synthesis of amides as used in peptide chemistry as described in e.g. Houben-Weyl, "Methoden der organischen Chemie", Vols. XV/1 and XV/2, Georg Thieme Verlag, Stuttgart, are also applicable.

Compounds of formula IV are described in the literature as for example in U.S. Pat. No. 2,680,731 and Goddard, C. J., et al., J. Heterocycl. Chem. 28 (1991) 17. These monoesters are usually prepared by selective saponification of the diester or oxidation of the corresponding aldehyde, but other methods may be useful as well and are well known to those skilled in the art.

(A-4) Compounds of formula I, wherein R$^1$ and R$^2$ have the meaning defined hereinbefore, can be prepared from compounds of formula V with hydroxylamine in the presence of a suitable base. The reaction is carried out in an inert solvent or diluent such as methanol or ethanol at temperatures between 0° C. and 100° C., conventionally at or near ambient temperature, and at a pH between 10 and 12. A suitable base is, for example, an alcoholate as e.g. sodium methylate or an inorganic base as e.g. potassium hydroxide. Instead of generating hydroxylamine in situ, it can be released separately and can be applied as a solution in an organic solvent, as for example an alcohol like methanol or ethanol.

(B) Another method for the preparation of compounds of the formula I is illustrated in the following reaction scheme 2:

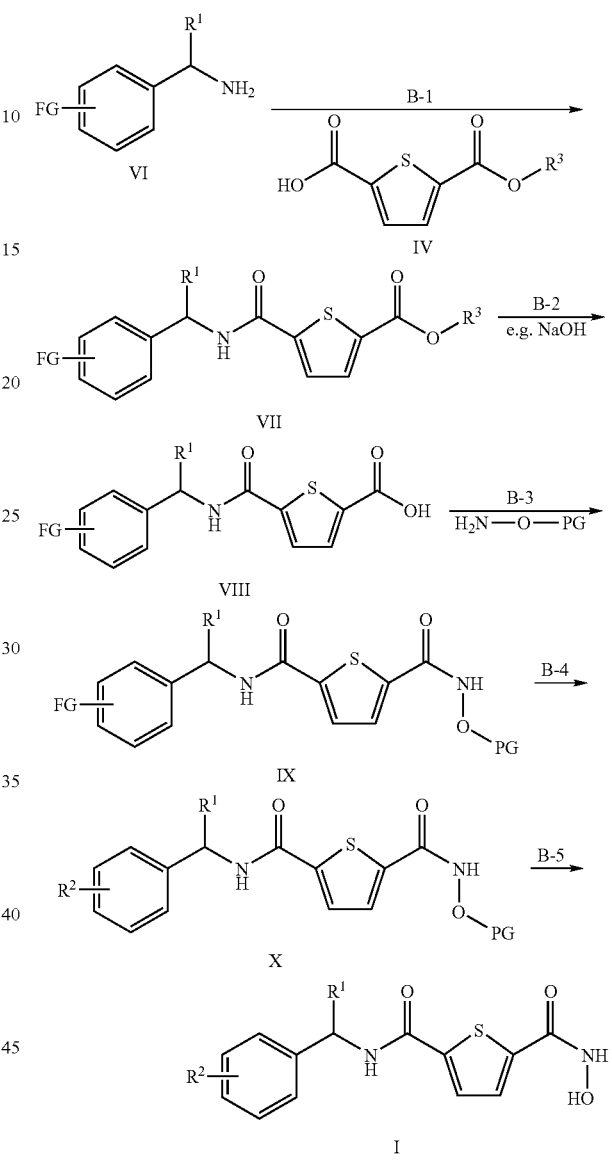

In scheme 2, R$^1$ and R$^2$ are defined as for formula I and R$^3$ is alkyl or optionally substituted benzyl. FG means a functional group like halogen. PG means a protecting group like benzyl-, p-methoxybenzyl-, tert-butyloxycarbonyl-, trityl-, or silyl groups such as the trimethylsilyl- or dimethyl-tert-butylsilyl group.

(B-1) Compounds of the formula VII can be obtained from compounds of the formula VI wherein R$^1$ has the meaning defined hereinbefore and FG is a suitable functional group, preferably a halogen, and compounds of formula VI wherein R$^3$ is alkyl or benzyl as described in section (A-3).

(B-2) Compounds of the formula VIII, wherein R$^1$ has the meaning defined hereinbefore, FG is a functional group, preferably a halogen, and R$^3$ is alkyl or benzyl, are prepared from compounds of the formula VII by hydrolysis. The conditions under which the hydrolysis is carried out depend on the nature of the group R³. When R³ is a methyl or ethyl group, the reaction is carried out in the presence of a base, for example, lithium hydroxide, sodium hydroxide, or potassium hydroxide in an inert solvent or diluent, for example, in methanol or ethanol. When R³ is a tert-butyl group, the reaction is carried out in the presence of an acid, for example, a solution of hydrochloric acid in an inert solvent such as diethyl ether or dioxane, or trifluoroacetic acid in dichloromethane. When R³ is a benzyl group, the reaction is carried out by hydrogenolysis in the presence of a noble metal catalyst such as palladium or platinum on a suitable carrier, such as carbon. Not necessarily all methods of hydrolysis are compatible with all groups R¹ and R². In cases where the features of these groups do not allow the usage of a certain method of hydrolysis, other methods of preparation need to be applied.

(B-3) Compounds of the formula IX, wherein R¹ has the meaning defined hereinbefore, FG is a suitable functional group, preferably a halogen, and PG refers to a suitable protecting group, are prepared from compounds of the formula VIII by treatment with an O-protected hydroxylamine. This reaction typically involves a two-step one-pot procedure.

In the first step, the carboxylic acid of the formula VIII is activated analogously to the acids of formula IV in section (A-3).

In the second step, the O-protected hydroxylamine is added to the solution, at the temperature used for the activation, and the temperature is slowly adjusted to ambient temperature. These methods are well known to those skilled in the art. In principle, all methods for the synthesis of amides as used in peptide chemistry as described in e.g. Houben-Weyl, "Methoden der organischen Chemie", Vols. XV/1 and XV/2 are also applicable.

Suitable protecting groups PG may be the benzyl-, p-methoxybenzyl-, tert-butyloxycarbonyl-, trityl-, or silyl groups such as the trimethylsilyl- or dimethyl-tert-butylsilyl group. The reactions carried out depend on the type of the protecting group. When the protecting group is a benzyl- or p-methoxybenzyl group, the reaction carried out is a hydrogenolysis in an inert solvent such as an alcohol like methanol or ethanol, in the presence of a noble metal catalyst such as palladium on a suitable carrier such as carbon, barium sulfate, or barium carbonate, at ambient temperature and pressure. When the protecting group is the tert.butyloxycarbonyl-, trityl-, or a silyl group such as the trimethylsilyl- or dimethyl-tert-butylsilyl-group, the reaction is carried out in the presence of acids at a temperature between −20° C. and 60° C., preferably between 0C and ambient temperature. The acid may be a solution of hydrochloric acid in an inert solvent such as diethyl ether or dioxane, or trifluoro acetic acid in dichloromethane. When the protecting group is a silyl group such as the trimethylsilyl or dimethyl-tert.butylsilyl group, the reaction can also be carried out in the presence of a fluoride source such as sodium fluoride or tetrabutyl ammonium fluoride in an inert solvent such as dichloromethane. Not necessarily all protecting groups PG are compatible with all groups R¹. In cases where the features of these groups don't allow the usage of a certain protecting group, other protecting groups Y or other methods of preparation need to be applied.

(B-4) Compounds of formula X, wherein R¹ and R² have the meaning defined hereinbefore, and PG refers to a suitable protecting group, e.g. halogen, especially iodide are prepared from compounds of the formula IX by treatment with arylthioles or benzyl-thioles as described in e.g. Shukla, V. G., et al., J. Org. Chem. 68 (2003) 5422-5425; Howbert, J. J., et al., Synthetic Commun. 20 (1990) 3193-3200, and Steven V. Ley, et al., Angew. Chem. Inter. Ed. 42 (2003) 5400.

(B-5) The final products of the general formula I, wherein R¹ and R² have the meaning defined hereinbefore, are obtained after deprotection of compounds of formula VII.

(C) Another method for the preparation of compounds of the formula I is the reaction of a compound of the formula XI (which are readily obtainable by hydrolysis of compounds of formula V; see section (B-2)) with hydroxylamine as illustrated within the following reaction scheme 3 wherein, R¹ and R² are defined as for formula I and R³ is alkyl or optionally substituted benzyl:

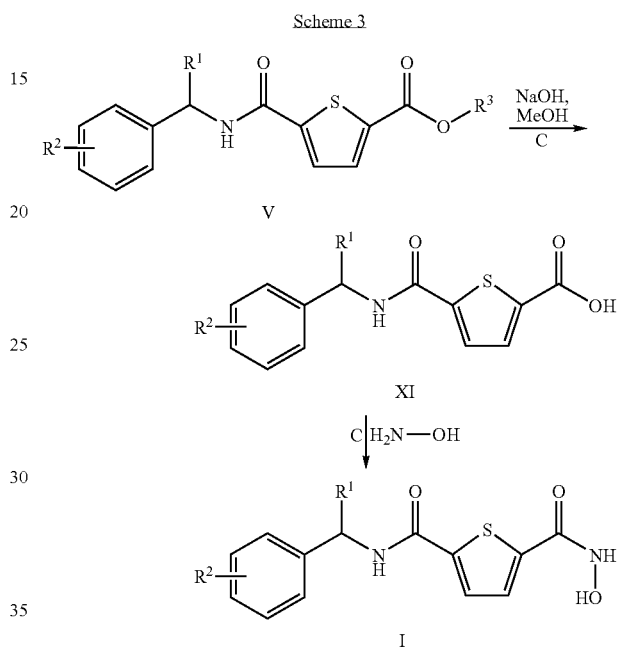

This reaction typically involves a two-step one-pot procedure.

In the first step, the carboxylic acid of the formula XI is activated analogously to the acids of formula IV in section (A-3).

In the second step, hydroxylamine is added to the solution, at the temperature used for the activation, and the temperature is slowly adjusted to ambient temperature. These methods are well known to those skilled in the art. In principle, all methods for the synthesis of amides as used in peptide chemistry as described in e.g. Houben-Weyl, "Methoden der organischen Chemie", Vols. XV/1 and XV/2 are also applicable.

(D) Compounds of formula I can also be prepared with methods of solid phase supported synthesis. 2,5-Thiophene-dicarboxylic acid is reacted with a hydroxylamine moiety (—O—NH2) bound to a resin, e.g. a Wang resin (Wang-O—NH2 resin, e.g. hydroxylamine Wang resin or hydroxylamine 2-chlorotrityl resin) to form a resin-bound hydroxamic acid. The second carboxylic acid moiety is reacted with amines of formula III, wherein R¹ and R² have the meaning defined hereinbefore, by standard methods of amide bond formation as described in e.g. Houben-Weyl, "Methoden der organischen Chemie", Vols. XV/1 and XV/2. After this, the hydroxamic acid is liberated from the solid support. This can be done for example with TFA. Typically, the cleavage of the hydroxamic acids is achieved by treatment of the resin with 50% TFA in dichloromethane in the presence of triisopropyl silane at ambient temperature. The crude products can be purified by LC-MS, if necessary.

Enantiomerically pure amines of the formula III in which $R^1$ and $R^2$ have the meaning defined hereinbefore can be prepared using different methods and thus serve as starting materials for the synthesis of pure enantiomers of compounds of the general formula I:

i. by standard procedures of synthetic chemistry as described e.g. in J. Am. Chem. Soc. 64 (1942) 477; Smith, H. E., et al., J. Am. Chem. Soc. 105 (1983) 1578-1584; Hanano, T., et al., Bioorg. Med. Chem. Lett. 10 (2000) 881-884, or Mukade, T., et al., J. Comb. Chem. 5 (2003) 590-596, starting from racemic amines of formula III in which $R^1$ and $R^2$ have the meaning defined hereinbefore ii. by separation of racemic amines of formula III in which $R^1$ and $R^2$ have the meaning defined hereinbefore into their enantiomers by known procedures as, for example, enzymatic resolution of racemates as described e.g. in Rasor, P. and Voss, E., Applied Catalysis A 221 (2001) 145-158, and Iglesias, L. E., et al., Tetrahedron: Asymmetry 8 (1997) 2675-2677;

iii. by separation of racemic amines of formula III in which $R^1$ and $R^2$ have the meaning defined hereinbefore into their enantiomers by chromatography on an analytical, semipreparative or preparative scale using suitable optically active stationary phases with suitable eluents. Suitable optically active stationary phases include, but are not limited to, silica (e.g. ChiraSper, Merck; Chiralpak OT/OP, Baker), cellulose esters or carbamates (e.g. Chiracel OB/OY, Baker) or others (e.g. Crownpak, Daicel or Chiracel OJ-R, Baker);

iv. by formation of diastereomeric compounds from compounds of formula III together with other optically active compounds, e.g. camphorsulfonic acid or brucin, and separation of these diastereomeric compounds, followed by the liberation from the optically active agent v. by enantioselective reduction of ketones of the general formula II using reagents as for example the Corey-Bakshi-Shibata reagent (see e.g. Corey, E. J., J. Am. Chem. Soc. 109 (1987) 7925-7926) and transformation of the formed, enantiomerically pure alcohols into the corresponding azides (inversion of stereo-configuration via Mitsunobu reaction) and subsequent reduction to the enantiomerically pure amines.

Another method for the preparation of pure enantiomers of compounds of the general formula I is the synthesis of racemic compounds according to methods (A), (B), (C), or (D) applying racemic amines of formula III in which $R^1$ and $R^2$ have the meaning defined hereinbefore. The racemates can be separated into both enantiomers either on the stage of the final products I or on the stage of the precursors V or X. The separation can be performed by chromatography on an analytical, semipreparative or preparative scale using suitable optically active stationary phases with suitable eluents. Suitable optically active stationary phases include, but are not limited to, silica (e.g. ChiraSper, Merck; Chiralpak OT/OP, Baker), cellulose esters or carbamates (e.g. Chiracel OB/OY, Baker) or others (e.g. Crownpak, Daicel or Chiracel OJ-R, Baker). Other methods for the separation of enantiomers can also be applied, like the formation of diastereomers from compounds of the formula I or the formula V together with other optically active compounds, e.g. camphorsulfonic acid or brucin, and separation of these diastereomeric compounds, followed by the liberation from the optically active agent.

Compounds of the present invention, wherein $R^2$ is an optionally halogenated alkylsulfinyl group, especially —S(O)—CF$_3$ and —S(O)—CH$_3$, or an optionally substituted phenyl-sulfinyl group or an optionally substituted benzyl-sulfinyl group, can be prepared by oxidation of the corresponding thioether derivatives. This oxidation reaction is preferably carried out in an inert solvent with oxidizing agents like peracids, e.g. 3-chloro-benzenecarboperoxoic acid in dichloromethane or 2-iodoxybenzoic acid in chloroform or iodosobenzene in toluene to yield the corresponding optionally halogenated alkylsulfinyl.

Oxidation to the corresponding sulfonyl derivatives requires more rigorous conditions, for example periodic acid in acetonitrile under catalysis of chromium(VI) oxide or oxone in aqueous methanol or excess of 3-chloro-benzenecarboperoxoic acid and prolonged reaction time.

An object of the present invention are pharmaceutical compositions containing a pharmacologically effective amount of one or more compounds of formula I in a mixture with pharmaceutically acceptable excipients and/or diluents.

According to a further aspect of the invention there is provided a medicament containing one or more compounds of the formula I as active ingredients together with pharmaceutically acceptable adjuvants. Such medicaments or pharmaceutical compositions may be in a form suitable for oral administration, for example as tablets, coated tablets, dragees, capsules, solutions emulsions or suspensions; for parenteral injections (including intravenous, subcutaneous, intramuscular, intravascular or infusion) as a sterile solution, suspension or emulsion; for topical administration as an ointment or cream or for rectal administration as a suppository. These pharmaceutical preparations can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions can comprise the following:

| Item | Ingredients | Mg/Tablet | |
|---|---|---|---|
| 1 | Compound of formula (I) | 25 | 100 |
| 2 | Anhydrous Lactose | 73 | 35 |
| 3 | Croscarmellose Sodium | 6 | 8 |
| 4 | Povidone K30 | 5 | 6 |
| 5 | Magnesium Stearate | 1 | 1 |
| | Total Weight | 140 | 150 |

Procedure:
1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.

5. Add the Item 5 to the milled granulation Step 4 and mix for 3 minutes.
6. Compress the granulation from Step 5 on a suitable press.

Another pharmaceutical preparation is e.g. a micro-suspension of the compounds according to formula I. To obtain said micro-suspension the following materials were used:

An aqueous solution of 7.5% modified gelatine XF 20 (Braun) per injection (dissolved, filtered with a pore size of 0.45 μm and autoclaved), filters (custom made, mesh size 100 μm), filter holder, coupling, washed glass beads with a diameter of 0.25 mm and heat sterilised Retsch mills.

For the preparation of a typical batch 6244 mg of a compound of formula (I) were weighted into two 50 ml bottle flasks with 30 g glass beads, dispersed with a spatulum and vortexed. Then 10 ml gelatine vehicle were added to each bottle. The bottles were vortexed, capped and wrapped in aluminium foil for light protection. The contents was milled for 14 hours at 30/s in a Retsch mill. The micro-suspension was then extracted from the beads with two layers of filter (100 μm) on a filter holder, coupled to a recipient vial by centrifugation at 400 g during two minutes and including six washing steps, to give a final volume of 130 ml.

After homogenisation, the content was determined by HPLC to be 45.7 mg/ml which corresponds to a yield of 95%. The micro-suspension was diluted with 18.6 ml to give a final concentration of 40 mg/ml. The obtained spherical, granule-like particles show diameters between 1 and 5 μm as determined by microscopy. For storage, the micro-suspension was filled into sterile vials, capped, labelled and kept at −20° C. Before use, the micro-suspension must be homogenised vigorously by vortex.

The hydroxamate of formula I will normally be administered to a warm-blooded animal at a unit dose within the range 5-5000 mg per square meter body area of the animal, i.e. approximately 0.1-100 mg/kg, and this normally provides a therapeutically-effective dose. A unit dose form such as a tablet or capsule will usually contain, for example 1-250 mg of active ingredient. Preferably a daily dose in the range of 1-100 mg/kg is employed. However the daily dose will necessarily be varied depending upon the host treated, the particular route of administration, and the severity of the illness being treated. Accordingly the optimum dosage may be determined by the practitioner who is treating any particular patient.

Pharmacological Activity

To show the activity of the compounds according to this invention, their effects on a human colon carcinoma cell line was evaluated using a standard MTT-assay. MTT (3-(4,5-dimethylthiazol-2-yl)-2,5-diphenyl tetrazolium bromide) is widely used for the quantitative determination of cytotoxic effects or in vitro chemosensitivity of tumor cells. The assay is based on the cleavage of the yellow tetrazolium salt (MTT) to purple formazan crystals by metabolic active cells. For details, see Rubinstein, L. V., et al., J. Natl. Cancer Inst. 82 (1990) 1113-1118.

We proceeded as follows: HT-29 cells (human colon carcinoma cell line, ATCC-No. HTB-38) were cultivated in RPMI 1640 medium with GlutaMAX™ I (Invitrogen, Cat-No. 61870-010), 2.5% fetal calf serum (FCS, Sigma Cat-No. F4135 (FBS)), 2 mM glutamine, 100 units/ml penicillin, 100 μg/ml streptomycin (=Pen/Strep from Invitrogen Cat. No. 15140). For the assay the cells were seeded in 384 well plates, 900 cells per well, in the same medium. At the next day, the compounds (dissolved 10 mM in DMSO) were added in various concentrations ranging from 30 μM to 1.5 nM. After 5 days, the MTT assay was done mainly according to the instructions of the manufacturer (Cell proliferation kit I, MTT, from Roche Molecular Biochemicals). In brief: MTT labeling reagent was added to a final concentration of 0.5 mg/ml, added and incubated for 4 hrs at 37° C., 5% CO2. During this incubation time purple formazan crystals are formed. After addition of the solubilization solution (20% Sodium Dodecyl Sulfate (SDS) in 0.02 M HCl) the plates were incubated overnight at 37° C., 5% CO2. After careful mixing, the plates were measured in Victor 2 (scanning multiwell spectrophotometer, Wallac) at 550 nm.

A decrease in number of living cells results in a decrease in the total metabolic activity in the sample. The decrease directly correlates to the amount of purple colour resulting from the solubilization of the purple formazan crystals. Determination of IC90 was done using XL-fit (XLfit software (ID Business Solution Ltd., Guilford, Surrey, UK)).

The reference compound has the following structure.

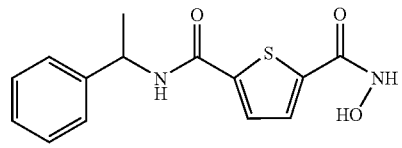

| Compounds according to this invention | IC90 HT29 [μM] |
| --- | --- |
| Reference compound | 1.12 |
| Example 2-2 | 0.21 |
| Example 3 | 0.22 |
| Example 1 | 0.34 |

To further demonstrate the activity of the compounds according to this invention as HDAC inhibitors, their effect on histone deacetylase inhibition was evaluated using the following biochemical quench assay:

The function of histone deacetylase (HDAC) is the deacetylation of lysines in e.g. histone H4. A peptide of 17 amino acids derived from histone H4 was labeled with tetramethylrhodamine (TAMRA, fluorophore, Invitrogen) at the C-terminus and $Q_SY$-7™ (quencher dye, Invitrogen) at the N-terminus and was used as a substrate (TAMRA—first 17 aa of histone H4—QSY7). Following deacetylation by HDAC, the enzyme Lys C is able to cleave the peptide after lysine. This results in a loss of the quench effect and a high fluorescence signal. Inhibition of HDAC by compounds results in low signals because Lys C could not cleave the substrate and the quench effect persists.

For dose response curves, 10 concentrations were diluted 1:3 starting at 30 μM. 10 μl compound dilution were put into each well of a 384 well plate. 10 μl HDAC were added (recombinant HDAC-1 purified from HEK 293 cells (human embryonic kidney cell line transformed by Adenovirus 5 fragments, ATCC-No. CRL 1573); enzyme activity has to be assessed for each preparation). 10 μl peptide substrate was added (1 μM final concentration, derived from 1 mM stock solution diluted 1:1000 in test buffer). After 90 min incubation at room temperature, the reaction was stopped by addition of 20 μl test buffer including 3 μg/ml Lys C and 0.075% Sodium Dodecyl Sulfate (SDS). After overnight incubation the fluorescence signal of TAMRA was measured (Victor 2 from Wallac, absorption 544 nm, emission 590 nm). The O.D. of DMSO (dimethylsulfoxide)-treated control wells is 100%, the % inhibition of compound treated wells is calculated in relation to 100%. Based on 10 concentrations an IC50 curve is generated by using XLfit3 (XLfit software (ID Business Solution Ltd., Guilford, Surrey, UK)).

Test buffer used: a mixture of 10 mM 4-(2-hydroxyethyl)-1-piperazineethanesulfonic acid (HEPES) pH8, 10 mM NaCl, 10% Glycerol, 0.005% Triton X100™, 0.1 mM ethylenediaminetetraacetic acid (EDTA), 0.1 mM Tris(2-carboxyethyl)phosphine (TCEP). Used plates: 384 well plates (black, Greiner, 781077).

The reference compound has the following structure.

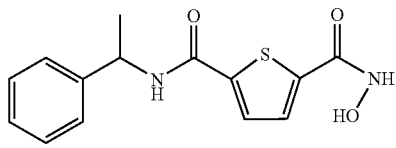

| Compounds according to this invention | $IC_{50}$ HDAC quench assay [nM] |
| --- | --- |
| Reference compound | 3.12 |
| Example 2-3 | 2.26 |
| Example 2-1 | 3.11 |

An embodiment of the present invention is a medicament, as defined hereinbefore, for the inhibition of tumor cell proliferation by induction of histone acetylation in said tumor cell.

Another embodiment of the present invention is a medicament, as defined hereinbefore, for the treatment of neoplasms of the hematopoetic and lymphatic system.

Still another embodiment of the present invention is a medicament, as defined hereinbefore, for the treatment of cancer.

Still another embodiment of the present invention is a medicament as defined herein before for the treatment of colon-, breast-, lung-, prostate-, rectal-, stomach-, bladder-, pancreatic- or ovarian cancer.

Yet another embodiment of the present invention is the use of one or more compounds of formula I for the manufacture of medicaments for the inhibition of tumor cell proliferation by induction of histone acetylation in said tumor cell.

Yet another embodiment of the present invention is the use of one or more compounds of formula I for the manufacture of medicaments for treatment of cancer.

Yet another embodiment of the present invention is the use of one or more compounds of formula I for the manufacture of medicaments for treatment of colon-, breast-, lung-, prostate-, rectal-, stomach-, bladder-, pancreatic- or ovarian cancer.

Yet another embodiment of the present invention is the use of one or more compounds of formula I for the manufacture of medicaments for treatment of neoplasms of the hematopoetic and lymphatic system.

Yet another embodiment of the present invention is a method for inhibiting tumor cell proliferation by induction of histone acetylation in a tumor cell, due to administering to said tumor cell an effective amount of one or more compounds of formula I. According to a further feature of this aspect of the invention there is provided a method for producing an anti-cell-proliferation effect in a warm-blooded animal, such as man, in need of such treatment which comprises administering to said animal an effective amount of an hydroxamate as defined hereinbefore.

Therefore, still another embodiment of the present invention is the method as described above, wherein the tumor is colon-, breast-, lung-, prostate-, rectal-, stomach-, bladder-, pancreatic- or ovarian cancer.

According to a more preferred aspect of the present invention there is provided a compound of the formula I as defined hereinbefore for use in a method of treatment of the human or animal body by therapy. We have now found that the said compounds of the present invention possess anti-cell-proliferation properties which are believed to arise from their histone deacetylase inhibitory activity. Accordingly the compounds of the present invention provide a method for treating the proliferation of malignant cells. Accordingly the compounds of the present invention are expected to be useful in the treatment of cancer by providing an anti-proliferative effect, particularly in the treatment of cancers of the breast, lung, colon, rectum, stomach, prostate, bladder, pancreas and ovary. It is in addition expected that a derivative of the present invention will possess activity against a range of leukemias, lymphoid malignancies and solid tumors such as carcinomas and sarcomas in tissues such as the liver, kidney, prostate and pancreas.

The anti-cell-proliferation treatment defined hereinbefore may be applied as a sole therapy or may involve, in addition to the hydroxamate of the invention, one or more other anti-tumor substances, for example those selected from, for example, mitotic inhibitors, for example vinblastine; alkylating agents, for example cis-platin, carboplatin and cyclophosphamide; inhibitors of microtubule assembly, like paclitaxel or other taxanes; antimetabolites, for example 5-fluorouracil, capecitabine, cytosine arabinoside and hydroxyurea, or, for example, intercalating antibiotics, for example adriamycin and bleomycin; immunostimulants, for example trastuzumab; DNA synthesis inhibitors, e.g. gemcitabine; enzymes, for example asparaginase; topoisomerase inhibitors, for example etoposide; biological response modifiers, for example interferon; and anti-hormones, for example antioestrogens such as tamoxifen or, for example antiandrogens such as (4'-cyano-3-(4-fluorophenylsulphonyl)-2-hydroxy-2-methyl-3'-(trifluoromethyl)-propionanilide, or other therapeutic agents and principles as described in, for example, Cancer: Principles & Practice of Oncology, Vincent T. DeVita, Jr., Samuel Hellmann, Steven A. Rosenberg; 5th ed., Lippincott-Raven Publishers, 1997. Such conjoint treatment may be achieved by way of the simultaneous, sequential or separate dosing of individual components of the treatment. According to this aspect of the invention there is provided a pharmaceutical product comprising a hydroxamate of the formula I as defined hereinbefore and an additional anti-tumor substance as defined hereinbefore for the conjoint treatment of cancer.

The following examples and references are provided to aid the understanding of the present invention, the true scope of which is set forth in the appended claims. It is understood that modifications can be made in the procedures set forth without departing from the spirit of the invention.

EXAMPLES

Example 1

Thiophene-2,5-dicarboxylic acid 2-hydroxyamide 5-{[1-(4-trifluoromethylsulfanyl-phenyl)-ethyl]-amide}

Step 1: Synthesis of 1-(4-Trifluoromethylsulfanyl-phenyl)-ethyl amine

To a mixture of 1.1 g (0.005 mol) 1-(4-trifluoromethylsulfanyl-phenyl)-ethanone and molecular sieves in 20 ml methanol, 3.9 g (0.05 mol) ammonium acetate and 315 mg (0.005 mol) sodium cyanoborohydride were added and the reaction mixture was stirred 2d (HPLC control) at 50° C. After cooling to room temperature (rt), the molecular sieves were filtered off and washed with methanol. The solvent of the combined filtrates was evaporated and dichloromethane and water were added to the residue. While stirring the mixture was acidified with 6N aqueous HCl solution. The aqueous phase was separated and the organic phase was extracted two times with 1N aqueous HCl solution. Ethyl acetate was added to the combined aqueous phases and the mixture was basified with 6N NaOH. The organic phase was separated and the aqueous phase was extracted two more times with ethyl acetate. The organic combined organic phases were dried over MgSO4 and the solvent evaporated at reduced pressure to afford the crude product, which was purified by flash chromatography using silica and an ethyl acetate/methanol/triethylamine eluent to affort 470 mg (0.0021 mol) 1-(4-trifluoromethylsulfanyl-phenyl)-ethylamine.

Step 2: Synthesis of 5-[1-(4-Trifluoromethylsulfanyl-phenyl)-ethylcarbamoyl]-thiophene-2-carboxylic acid methyl ester To a solution of 395 mg (2.1 mmol) thiophene-2,5-dicarboxylic acid monomethyl ester in 15 ml dichloromethane, 428 mg (2.5 mmol) N'-(3-dimethylaminopropyl)-N-ethylcarbodiimide hydrochloride were added. After 30min at room temperature 470 mg (2.1 mmol) 1-(4-trifluoromethylsulfanyl-phenyl)-ethylamine in 5 ml dichloro-methane were added. The reaction mixture was stirred for 5 h and then extracted with aqueous 1N HCl, with saturated aqueous NaHCO$_3$ solution and with water. The organic phase was dried over MgSO$_4$ and the solvent was evaporated. The crude product was purified by flash chromatography using silica and a dichloro-methane/methanol eluent to affort 360 mg (0.92 mmol) 5-[1-(4-trifluoromethylsulfanyl-phenyl)-ethylcarbamoyl]-thiophene-2-carboxylic acid methyl ester.

Step 3: Synthesis of Thiophene-2,5-dicarboxylic acid 2-hydroxyamide 5-{[1-(4-trifluoromethylsulfanyl-phenyl)-ethyl]-amide}

To a solution of 60 mg (0.15 mmol) 5-[1-(4-trifluoromethylsulfanyl-phenyl)-ethylcarbamoyl]-thiophene-2-carboxylic acid methyl ester in 10 ml methanol, 0.77 ml (1.5 mmol) of a 2M solution of hydroxylamine in methanol and 10 mg (0.15 mmol) potassium hydroxide in little methanol were added. After 4 h at rt, the reaction mixture was filtered and the solid was washed with methanol. The filtrate was treated with dry ice to lower the pH value to almost neutral. Stirring was continued for 15 min and the formed precipitate was filtered off. The solid was washed with methanol and the solvent of the combined organic filtrates was evaporated. The residue was purified by preparative reversed phase chromatography to yield 11 mg (0.028 mmol) thiophene-2,5-dicarboxylic acid 2-hydroxyamide 5-{[1-(4-trifluoromethylsulfanyl-phenyl)-ethyl]-amide} (compound 1).

Compound 1: calculated MW 390.41, found MW (M+H) 391.0; 1H-NMR (400 MHz, d6-DMSO): δ=8.81 (d, 1H), 7.74-7.66 (m, 3H), 7.55-7.51 (m, 2H), 7.21 (m, 1H), 5.14 (m, 1H), 1.48 (d, 3H)

Example 2

According to the preparation procedure of example 1, the following thiophene hydroxamic acid derivatives of the general formula I have been prepared starting from the appropriate phenylalkylketone:

| no. | name | calc. MW | found MW (M + H) | 1H-NMR (400 MHz; d6-DMSO) |
| --- | --- | --- | --- | --- |
| 2-1 | Thiophene-2,5-dicarboxylic acid 2-hydroxyamide 5-{[1-(4-trifluoromethoxy-phenyl)-ethyl]-amide} | 374.34 | 375.27 | δ = 11.35 (bs, 1H), 9.24 (bs, 1H), 8.98 (d, 1H), 7.82 (m, 1H), 7.58 (m, 1H), 7.49 (m, 2H), 7.33 (m, 2H), 5.14 (m, 1H), 1.48 (d, 3H) |
| 2-2 | Thiophene-2,5-dicarboxylic acid 2-hydroxyamide 5-{[1-(3-trifluoromethylsulfanyl-phenyl)-ethyl]-amide} | 390.41 | 390.9 | δ = 11.33 (bs, 1H), 9.24 (bs, 1H), 9.03 (d, 1H), 7.83 (m, 1H), 7.72 (m, 1H), 7.64-7.56 (m, 3H), 7.54-7.48 (m, 1H), 5.16 (m, 1H), 1.49 (d, 3H) |
| 2-3 | Thiophene-2,5-dicarboxylic acid 2-hydroxyamide 5-{[1-(4-methylsulfanyl-phenyl)-ethyl]-amide} | 336.43 | 337.20 | δ = 11.35 (bs, 1H), 9.24 (bs, 1H), 8.91 (d, 1H), 7.81 (m, 1H), 7.56 (m, 1H), 7.35-7.29 (m, 2H), 7.26-7.21 (m, 2H), 5.07 (m, 1H), 3.33 (s, 3H), 1.46 (d, 3H) |
| 2-4 | Thiophene-2,5-dicarboxylic acid 2-{[1-(4-benzenesulfonyl-phenyl)-ethyl]-amide} 5-hydroxyamide | 430.50 | 429.20 (M − H) | δ = 11.35 (bs, 1H), 9.23 (bs, 1H), 9.01 (d, 1H), 7.98-7.90 (m, 4H), 7.80 (m, 1H), 7.72-7.65 (m, 1H), 7.63-7.52 (m, 5H), 5.13 (m, 1H), 1.46 (d, 3H) |

Example 3

Thiophene-2,5-dicarboxylic acid 2-hydroxyamide 5-{[1-(3-trifluoromethoxy-phenyl)-ethyl]-amide}

Step 1: Synthesis of 1-(3-Trifluoromethoxy-phenyl)-ethyl amine

An Emrys Process Vial (2-5 ml) was charged with 420 mg (2 mmol) of 1-(4-trifluoromethoxy-phenyl)-ethanone, ammonium acetate in MeOH (4.0 ml of a 5 M solution, 20 mmol) and sodium cyanoborohydride in MeOH (0.440 ml of a 5 M solution, 2.2 mmol). The reaction vessel was sealed and heated to 120° C. for 5 min in an Emrys Optimizer. After cooling and manual release of remaining pressure the vessel was uncapped and the reaction mixture concentrated at reduced pressure. The residue was dissolved in $Et_2O$ (10 ml) and extracted with 2 M aqueous HCl (3×5 ml). The combined aqueous phases were adjusted to pH 9 with a 10 M aqueous KOH and extracted with $CH_2Cl_2$ (4×10 ml). The combined organic phases were dried over $MgSO_4$ and the solvent evaporated at reduced pressure to afford 1-(3-trifluoromethoxy-phenyl)-ethyl amine which is used as crude product for step 2.

Step 2: Synthesis of 5-[1-(3-Trifluoromethoxy-phenyl)-ethylcarbamoyl]-thiophene-2-carboxylic acid methyl ester The title compound was prepared in an analogous manner to that described in example 1, step 2 from 1-(3-trifluoromethoxy-phenyl)-ethyl amine and thiophene-2,5-dicarboxylic acid monomethyl ester.

Step 3: Synthesis of Thiophene-2,5-dicarboxylic acid 2-hydroxyamide 5-{[1-(3-trifluoromethoxy-phenyl)-ethyl]-amide}

The title compound was prepared in an analogous manner to that described in example 1, step 3 from 5-[1-(3-trifluoromethoxy-phenyl)-ethylcarbamoyl]-thiophene-2-carboxylic acid methyl ester. Compound 3: calculated MW 374.34, found MW (M+H) 375.10; 1H-NMR (400 MHz, d6-DMSO): δ=11.36 (bs, 1H), 9.24 (bs, 1H), 8.99 (d, 1H), 7.82 (m, 1H), 7.59 (m, 1H), 7.50-7.39 (m, 2H), 7.35 (m, 1H), 7.26-7.21 (m, 1H), 5.16 (m, 1H), 1.48 (d, 3H)

LIST OF REFERENCES

Alo, B. I., et al. J. Chem. Soc., Perkin Trans. 1 (1990) 1611-1614
Bastin, R. J., et al., Organic Proc. Res. Dev. 4 (2000) 427-435 Corey, E. J., J. Am. Chem. Soc. 109 (1987) 7925-7926
DeVita, V. T. Jr., Hellmann, S., and Rosenberg, S. A., Cancer: Principles & Practice of Oncology, 5th ed., Lippincott-Raven Publishers (1997)
Gilman, H., et al., J. Am. Chem. Soc. 51 (1929) 3501-3508
Goddard, C. J., et al., J. Heterocycl. Chem. 28 (1991) 17
Hanano, T., et al., Bioorg. Med. Chem. Lett. 10 (2000) 881-884
Houben-Weyl, "Methoden der organischen Chemie", Vols. XV/1 and XV/2, Georg Thieme Verlag, Stuttgart
Howbert, J. J., et al., Synthetic Commun. 20 (1990) 3193-3200
Iglesias, L. E., et al., Tetrahedron: Asymmetry 8 (1997) 2675-2677
Koyama, Y., et al., Blood 96 (2000) 1490-1495
Ley, S. V., et al., Angew. Chem. Inter. Ed. 42 (2003) 5400-5449
Marks, P. A., et al., J. Nat. Cancer Inst. 92 (2000) 1210-1216
Marquie, J., et al., J. Org. Chem. 66 (2001) 421-425
Mukade, T., et al., J. Comb. Chem. 5 (2003) 590-596
Rasor, P., and Voss, E., Applied Catalysis A 221 (2001) 145-158
Rubinstein, L. V., et al., J. Natl. Cancer Inst. 82 (1990) 1113-1118
Shukla, V. G., et al., J. Org. Chem. 68 (2003) 5422-5425
Smith, H. E., et al., J. Am. Chem. Soc. 105 (1983) 1578-1584
Stahl, P. H., and Wermuth, G., (editors), Handbook of Pharmaceutical Salts, Verlag Helvetica Chimica Acta (VHCA), Zürich (2002)
Sun, X. H., et al., Synthetic Commun. 28 (1998) 1785-1791
Synth. Commun. 28 (1998) 4067
U.S. Pat. No. 2,680,731
U.S. Pat. No. 5,369,108
WO 98/55449
WO 01/38322
WO 01/70675
WO 02/22577
WO 03/011851
WO 2004/013130
WO 03/075929
WO 03/076395
WO 03/076400
WO 03/076401
WO 03/076421
WO 03/087066
WO 03/066579

The invention claimed is:

1. The compounds of formula I:

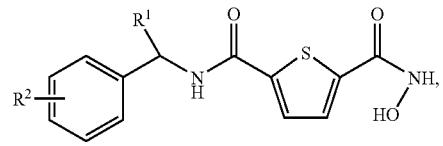

formula I wherein:
(a) $R^1$ is alkyl, which is optionally substituted one or more times by halogen; and
(b) $R^2$ is selected from the group consisting of:
 (1) —$SF_5$;
 (2) —O-alkyl; wherein the alkyl group is optionally substituted one or more times by halogen;
 (3) —$S(O)_2$—$CF_3$;
 (4) —S(O)-alkyl;
 (5) —S-alkyl; wherein the alkyl group is substituted one or more times by halogen;
 (6) —$S(O)_2$-aryl;
 (7) —S(O)-aryl;
 (8) —S-aryl;
 (9) —$S(O)_2$-benzyl;
 (10) —S(O)-benzyl; and
 (11) —S-benzyl;

and the pharmaceutically acceptable salts and the (R)- and (S)-enantiomers thereof.

2. The compounds of claim 1 wherein $R^1$ is methyl.
3. The compounds of claim 1, wherein $R^2$ is —O-alkyl; wherein the alkyl group is substituted one or more times by halogen.
4. The compounds of claim 1, wherein $R^2$ is —S-alkyl; wherein the alkyl group is optionally substituted one or more times by halogen.
5. The compounds of claim 1, wherein $R^2$ is selected from the group consisting of:
 (a) —O-alkyl wherein the alkyl group is substituted one to three times by fluorine; and (b) —S-alkyl wherein the alkyl group is substituted one to three times by fluorine.

6. The compounds of claim 1, wherein $R^2$ is —O—$CF_3$ or —O—$CHF_2$.

7. The compounds of claim 1, wherein $R^2$ is —$OCF_3$.

8. The compounds of claim 1, wherein $R^2$ is —$SCF_3$.

9. The compounds of claim 1, wherein $R^2$ is —$SCH_3$.

10. The compounds of claim 1 wherein $R^2$ is —$S(O)_2$-aryl.

11. The compounds of claim 1 wherein $R^2$ is —$S(O)_2$-phenyl.

12. The compounds of claim 1 wherein $R^1$ is ethyl.

13. A compound of claim 1 wherein the compound is Thiophene-2,5-dicarboxylic acid 2-hydroxyamide 5-{[1-(4-trifluoromethylsulfanyl-phenyl)-ethyl]-amide}.

14. A compound of claim 1 wherein the compound is Thiophene-2,5-dicarboxylic acid 2-hydroxyamide 5-{[1-(4-trifluoromethoxy-phenyl)-ethyl]-amide}.

15. A compound of claim 1 wherein the compound is Thiophene-2,5-dicarboxylic acid 2-hydroxyamide 5-{[1-(3-trifluoromethylsulfanyl-phenyl)-ethyl]-amide}.

16. A compound of claim 1 wherein the compound is Thiophene-2,5-dicarboxylic acid 2-hydroxyamide 5-{[1-(4-methylsulfanyl-phenyl)-ethyl]-amide}.

17. A compound of claim 1 wherein the compound is Thiophene-2,5-dicarboxylic acid 2-{[1-(4-benzenesulfonyl-phenyl)-ethyl]-amide} 5-hydroxyamide.

18. A compound of claim 1 wherein the compound is Thiophene-2,5-dicarboxylic acid 2-hydroxyamide 5-{[1-(3-trifluoromethoxy-phenyl)-ethyl]-amide}.

19. A process for the manufacture of the compounds of claim 1 comprising:
(a) reacting compounds of formula IV:

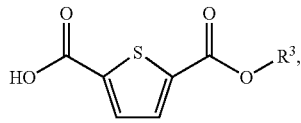

formula IV wherein $R^3$ is an alkyl group;
with racemic, or enantiomerically pure (R)-amines or (S)-amines of formula III:

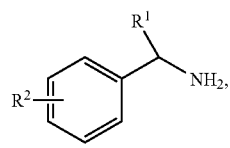

formula III wherein $R^1$ and $R^2$ are defined as in claim 1,
in the presence of a suitable activating agent,
to obtain the compounds of formula V:

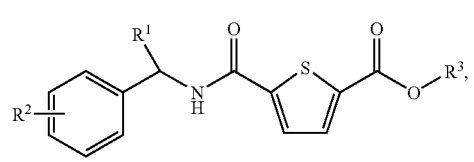

formula V wherein $R^1$ and $R^2$ are defined as in claim 1 and $R^3$ is alkyl, (b) subsequently treating said compounds of formula V with hydroxyl amine to obtain the compounds of formula I in claim 1; and (c) optionally transforming said compounds into their pharmaceutically acceptable salts.

20. A pharmaceutical composition comprising a compound of claim 1 and one or more pharmaceutically acceptable excipients, diluents, or adjuvants.

* * * * *

UNITED STATES PATENT AND TRADEMARK OFFICE
CERTIFICATE OF CORRECTION

PATENT NO. : 7,638,553 B2
APPLICATION NO. : 11/628725
DATED : December 29, 2009
INVENTOR(S) : Fertig et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 478 days.

Signed and Sealed this

Ninth Day of November, 2010

David J. Kappos
*Director of the United States Patent and Trademark Office*